United States Patent
Ra et al.

(10) Patent No.: US 10,172,347 B2
(45) Date of Patent: Jan. 8, 2019

(54) COMPOSITION FOR IMPROVING STABILITY OF STEM CELLS

(71) Applicant: Jeong Chan Ra, Chungcheongbuk-do (KR)

(72) Inventors: Jeong Chan Ra, Chungcheongbuk-do (KR); Sang Kyu Woo, Gyeonggi-do (KR)

(73) Assignee: Jeong Chan Ra, Chungcheongbuk-Do (KR)

( * ) Notice: Subject to any disclaimer, the term of this patent is extended or adjusted under 35 U.S.C. 154(b) by 0 days.

(21) Appl. No.: 15/126,231

(22) PCT Filed: Jan. 21, 2015

(86) PCT No.: PCT/KR2015/000595
§ 371 (c)(1),
(2) Date: Sep. 14, 2016

(87) PCT Pub. No.: WO2016/006782
PCT Pub. Date: Jan. 14, 2016

(65) Prior Publication Data
US 2017/0105406 A1    Apr. 20, 2017

(30) Foreign Application Priority Data

Jul. 8, 2014  (KR) .................. 10-2014-0085020

(51) Int. Cl.
| | |
|---|---|
| A01N 1/02 | (2006.01) |
| A61K 35/35 | (2015.01) |
| A61K 47/42 | (2017.01) |
| A61K 47/46 | (2006.01) |
| A61K 9/00 | (2006.01) |
| C12N 5/0775 | (2010.01) |

(52) U.S. Cl.
CPC .............. *A01N 1/02* (2013.01); *A01N 1/021* (2013.01); *A61K 9/0019* (2013.01); *A61K 35/35* (2013.01); *A61K 47/42* (2013.01); *A61K 47/46* (2013.01); *C12N 5/0667* (2013.01)

(58) Field of Classification Search
CPC ........ A01N 1/02; A01N 1/021; C12N 5/0667; A61K 47/46; A61K 35/35; A61K 9/0019; A61K 47/42
See application file for complete search history.

(56) References Cited

U.S. PATENT DOCUMENTS

| | | | | |
|---|---|---|---|---|
| 5,827,640 A * | 10/1998 | Wiggins | ................. | A01N 1/02 435/1.1 |
| 2010/0196329 A1 | 8/2010 | Ra et al. | | |
| 2010/0272694 A1 * | 10/2010 | Yang | ................. | A01N 1/0221 424/93.7 |

FOREIGN PATENT DOCUMENTS

| | | | |
|---|---|---|---|
| EP | 1820852 A1 | 8/2007 | |
| JP | 2000-119101 A | 4/2000 | |
| JP | 2009-514950 A | 4/2009 | |
| JP | 2010-528107 A | 8/2010 | |
| JP | 2012-510521 A | 5/2012 | |
| KR | 10-0394430 B1 | 7/2003 | |
| KR | 1020080103637 | * 11/2008 | ............. A61K 35/28 |
| KR | 10-2012-0055934 A | 6/2012 | |
| KR | 10-2012-0057784 A | 6/2012 | |
| KR | 10-2014-0046690 A | 4/2014 | |
| KR | 10-2014-0059988 A | 5/2014 | |
| RU | 2303631 C | 7/2007 | |
| WO | 9400567 A1 | 1/1994 | |
| WO | 2008147057 A | 12/2008 | |
| WO | 2012074265 A | 6/2012 | |

OTHER PUBLICATIONS

Tekkatte et al. "Humanized" Stem Cell Culture Techniques: The Animal Serum Controversy. Stem Cells International vol. 2011, Article ID 504723, 14 pages.*
Alencar et al. Cryopreservation of peripheral blood stem cell: the influence of cell concentration on cellular and hematopoietic recovery. Transfusion 2010;50:2402-2412 (Year: 2010).*
Baust et al. Cryopreservation An emerging paradigm change. Organogenesis 5:3, 90-96; Jul./Aug./Sep. 2009 (Year: 2009).*
DMEM product information. Sigma-Aldrich. www.sigmaaldrich.com/content/dam/sigma-aldrich/docs/Sigma/Formulation/d5796for.pdf. 2018. p. 1-3 (Year: 2018).*
Van Buskirk et al. Hypothermic Storage and Cryopreservation: Successful Short- and Long-Term Preservation of Cells and Tissues. BioProcess International Nov. 2004. p. 1-6 (Year: 2004).*
Aryal. Difference between Serum and Plasma . Microbiology Info. com p. 1-5 (Year: 2018).*
Cousin, B., et al., "Reconstitution of Lethally Irradiated Mice by Cells Isolated from Adipose Tissue", "Biochem. Biophys. Res. Commun.", Jan. 8, 2003, pp. 1016-1022, vol. 301.
Gronthos, S., et al., "Surface Protein Characterization of Human Adipose Tissue-Derived Stromal Cells", "Journal of Cellular Physiology", May 25, 2001, pp. 54-63, vol. 189.
Jiang, Y., et al., "Pluripotency of Mesenchymal Stem Cells Derived from Adult Marrow", "Nature", Jun. 20, 2002, pp. 41-49, vol. 418, Publisher: Nature Publishing Group.

(Continued)

*Primary Examiner* — Taeyoon Kim
(74) *Attorney, Agent, or Firm* — Hultquist, PLLC; Steven J. Hultquist

(57) ABSTRACT

The present invention relates to a composition capable of improving storage stability of stem cells. More specifically, the present invention relates to a composition which contains a serum or a plasma for improving cold storage stability of stem cells. The composition for improving storage stability of stem cells according to the present invention can maintain a survival rate of over 90% for at least 9 days without changes in the properties, the number or the size of the stem cells, and thus is useful in the long-term transport of stem cells for cell therapy and the preparation of cell therapeutics injection products having an excellent effect.

4 Claims, 6 Drawing Sheets

(56) References Cited

OTHER PUBLICATIONS

Miranville, A., et al., "Improvement of Postnatal Neovascularization by Human Adipose Tissue-Derived Stem Cells", "Circulation", Jul. 20, 2004, pp. 349-355, vol. 110.

Rodriguez, A., et al., "Adipocyte Differentiation of Multipotent Cells Established from Human Adipose Tissue", "Biochemical and Biophysical Research Communications", Mar. 5, 2004, pp. 255-263, vol. 315, No. 2.

Seo, M., et al., "Differentiation of Human Adipose Stromal Cells into Hepatic Lineage in vitro and in vivo", "Biochemical and Biophysical Research Communications", Jan. 6, 2005, pp. 258-264, vol. 328, No. 1.

Verfaillie, C., "Adult Stem Cells: Assessing the Case for Pluripotency", "Trends in Cell Biology", Sep. 26, 2002, pp. 502-508, vol. 12, No. 11.

Zuk, P., et al., "Multilineage Cells from Human Adipose Tissue: Implications for Cell-Based Therapies", "Tissue Engineering", Apr. 2001, pp. 211-228, vol. 7, No. 2.

"Extended European Search Report for EP15818206.3", dated Nov. 15, 2017.

"JPO Office Action, dated Oct. 13, 2017 for JP 2016-569967".

"JPO Office Action, dated Oct. 13, 2017 for JP Patent Application 2016-569967", , Page(s) Eng Trans.

Kohsaki, M., et al., "Non-Frozen Preservation of Committed Ematopoietic Stem Cells from Normal Human Bone Marrow", "Stem Cells", 1981, pp. 111-123, vol. 1.

Kohsaki, M., et al., "Medical Development: Liquid Storage of Human Hematopoietic Stem Cell", 1992, pp. 410-412, vol. 161, No. 6.

Kohsaki, M., et al., "Medical Development: Liquid Storage of Human Hematopoietic Stem Cell", 1992, Page(s) Eng Abst, vol. 161, No. 6.

"KIPO Office Action, dated Aug. 28, 2015 for KR Patent Application 10-2014-0148485".

"KIPO Office Action, dated Nov. 25, 2014 for KR Patent Application 10-2014-0148485".

"KIPO Office Action, dated Jun. 16, 2015 for KR Patent Application 10-2014-0148485".

Matsumoto, N., et al., "Sucessful Liquid Storage of Peripheral Stem Blood Cells at Subzero Non-Freezing Temperature", "Bone Marrow Transplantation", 2002, pp. 777-784, vol. 30, Publisher: Nature Publishing Group.

* cited by examiner

COMPOSITION FOR IMPROVING STABILITY OF STEM CELLS

CROSS-REFERENCE TO RELATED APPLICATIONS

This is a U.S. national phase under the provisions of 35 U.S.C. § 371 of International Patent Application No. PCT/KR15/00595 filed Jan. 21, 2015, which in turn claims priority of Korean Patent Application No. 10-2014-0085020 filed Jul. 8, 2014. The disclosures of such international patent application and Korean priority patent application are hereby incorporated herein by reference in their respective entireties, for all purposes.

TECHNICAL FIELD

The present invention relates to a composition for improving storage stability of stem cells, and more specifically, to a composition for improving cold-storage stability of stem cells containing blood serum or blood plasma.

BACKGROUND ART

Stem cells refer to cells capable of differentiating into at least two cells while having self-replicating ability and may be classified into totipotent stem cells, pluripotent stem cells, and multipotent stem cells.

Totipotent stem cells are cells having totipotent properties capable of developing into one perfect individual, and these properties are possessed by cells that have up to eight-cell stages after fertilization of an egg and a sperm. When these cells are isolated and transplanted into the uterus, these cells may develop into one complete individual. Pluripotent stem cells, which are cells capable of developing into various cells and tissue derived from the ectodermal, mesodermal and endodermal layers, are derived from an inner cell mass located inside of blastocysts generated after 4-5 days of fertilization. These cells are called "embryonic stem cells" and may differentiate into various other tissue cells, but do not form new living organisms. Multipotent stem cells are stem cells capable of differentiating into only cells specific to tissue and organs containing these cells.

Multipotent stem cells were first isolated from an adult bone marrow (Y. Jiang et al., *Nature*, 418:41, 2002), and thereafter, they were confirmed in several other adult tissue (C. M. Verfaillie et al., *Trends Cell Biol.* 12:502, 2002). However, stem cells in adult tissue such as bone marrow are very rarely present, and it is difficult to culture these cells without differentiation induction, and accordingly, it is difficult to culture these cells without specifically screened media. That is, there is disadvantage in that it is very difficult to isolate the stem cells and preserve the cells in vitro.

Recently, it was found that adipose tissue are new sources of multipotent stem cells (B. Cousin et al., BBRC, 301:1016, 2003; A. Miranville et al., *Circulation*, 110:349, 2004; S. Gronthos et al., *J. Cell Physiol.* 189:54, 2001; M. J. Seo et al., BBRC, 328:258, 2005), and it was reported that undifferentiated cell populations are included in human adipose tissue obtained by adipose extraction (liposuction), and have differentiation potency into adipose cells, bone forming cells, myoblast, and chondroblast in vitro (P. A. Zuk et al., *Tissue Eng.* 7:211, 2001; A. M. Rodriguez et al., *BBRC*, 315:255, 2004). In addition, it has been known through animal model experiments that adipose tissue-derived cells have a muscle regeneration ability and an ability to promote neurovascular differentiation. The adipose tissue has an advantage of being able to be extracted in a large amount, and accordingly, it has received attention as a new source of stem cells complementing the existing disadvantages.

The stem cells capable of being obtained in a large amount have been increasingly used as a cell therapeutic agent for injecting the stem cells themselves for the main purpose of medicine fields including treatment of incurable diseases, etc., and beauty, cosmetic, etc.

The stem cells for the purpose of the cell therapeutic agent have no problem when medical procedure is directly available to patients after culturing the stem cells. However, when it is required to control time for a medical procedure of stem cells depending on a patient's condition, long-term storage is required after culturing the stem cells. In addition, even when long-distance transport up to a place for practicing the cultured stem cells is required, it is essential to stably supply the stem cells. To this end, it is required to maintain a high survival rate of stem cells for a long period of time for about 5 to 10 days. However, currently, when the stem cells are maintained for a long period of time without freezing, there is a problem in that a cell survival rate is remarkably low. Meanwhile, a cell freezing method causes a remarkably deteriorated cell survival rate when thawed, and has problems on functionality, etc., as the stem cells from a biological perspective. In addition, transport in a freezing state is more difficult than transport in a refrigeration state.

As the conventional current technology of preserving the stem cells in the refrigeration state, there is a technology of suspending and storing human adipose tissue-derived mesenchymal stem cells in saline under refrigeration condition, but in this case, it is difficult to have a survival rate of 70% or more when storing the cells for 48 hours or more. It was confirmed that when sucrose or albumin is added to overcome the difficulty, the survival rate is 70% or more up to 48 hours to 72 hours, and storage stability is improved (Korean Patent Laid-Open Publication No. 10-2008-0103637). However, after 72 hours, since the survival rate is rapidly reduced, it is required to develop a composition for improving storage stability under refrigeration condition (4° C.) so that the survival rate of the stem cells included in cell therapeutic agents is stably maintained to be high for a long period of time.

Therefore, the present inventors made an effort to maintain the survival rate of the stem cells to be high even for a long-time cold-storage, and as a result, found that when blood serum or blood plasma is contained, the survival rate of the stem cell in a refrigeration state is maintained to be high for at least 9 days, and completed the present invention. There is a case in which human blood serum is used as a medium composition for cell culture (Korean Patent No. 10-0394430); however, a composition for improving storage stability of stem cells containing human blood serum or human blood plasma has not been disclosed.

DISCLOSURE OF INVENTION

An object of the present invention is to provide a composition for improving cold-storage stability of stem cells containing blood serum or blood plasma having a content of 5 to 80% (v/v).

Another object of the present invention is to provide a cell therapeutic injection product containing the composition as described above.

In order to achieve the foregoing objects, the present invention provides a composition for improving cold-storage stability of stem cells containing blood serum or blood plasma having a content of 5 to 80% (v/v).

The present invention also provides a cell therapeutic injection product containing the composition as described above.

BEST MODE

Figure 1:
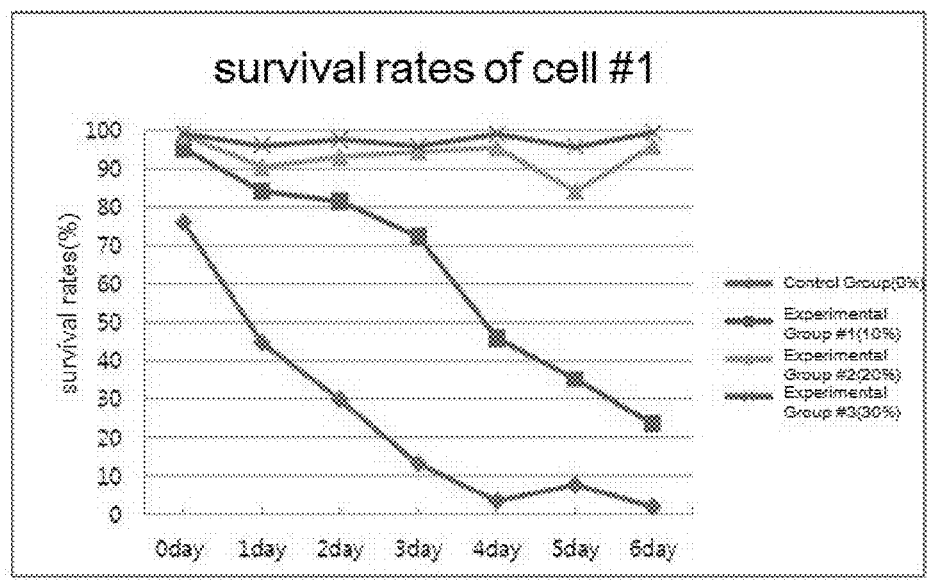
FIG. 1 illustrates comparison of survival rates of $0.5 \times 10^7$ stem cells according to the retention time from 0 to 144 hours, after cold-storage of the stem cells with different concentrations (10, 20, and 30%) of autologous sera and a preservative containing 0.3% albumin. The Control Group used a preservative containing 0.3% albumin.
Figure 2:
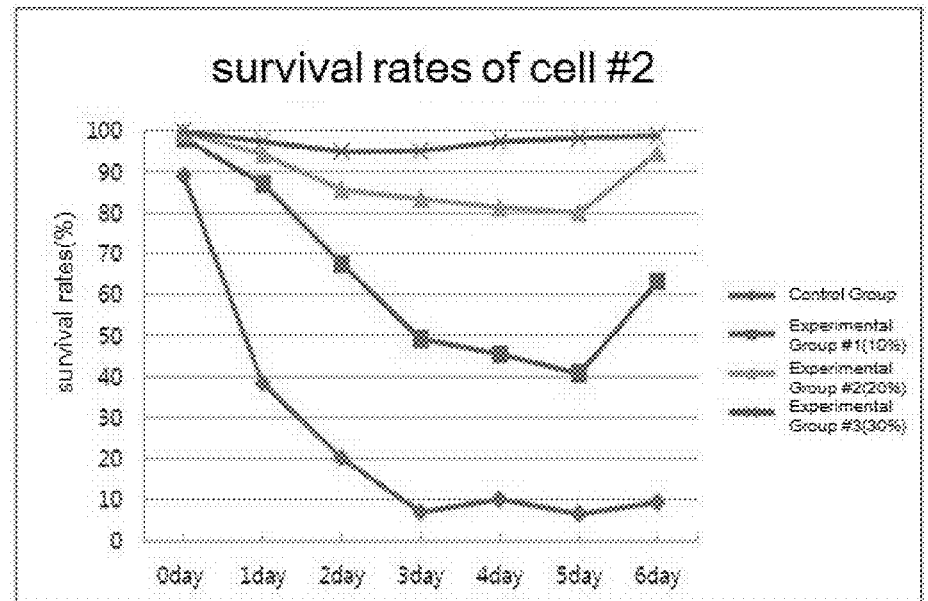
FIG. 2 illustrates comparison of survival rates of $1.0 \times 10^7$ stem cells according to the retention time from 0 to 144 hours, after cold storing the stem cells with different concentrations (10, 20, and 30%) of autologous sera and a preservative containing 0.3% albumin. The Control Group used a preservative containing 0.3% albumin.

Unless defined otherwise, all the technical and scientific terms used herein have the same meanings as those generally understood by persons skilled in the art to which the present invention pertains. Generally, the nomenclature used herein are well known and commonly employed in the art.

In the present invention, it was found that 95% or more of the survival rate of stem cells in a refrigeration state is maintained by a stem cell preservative containing the blood serum or the blood plasma, such that storage stability of the stem cells is improved. The stem cell preservative containing the blood serum or the blood plasma according to the present invention is capable of maintaining the survival rate of stem cells in a refrigeration state to be high for at least 9 days, which is useful to stably supply stem cells for cell therapy.

As used herein, the term "cell therapeutic injection product" or "cell therapeutic agent" means a pharmaceutical composition capable of containing stem cells to treat defects of tissue and being injected for parenteral administration, i.e., as an injection form, in a defect site or an adjacent part thereof, thereby correcting the defects.

As used herein, the term "excipient" refers to a material added with a predetermined volume and weight for facilitating the handling, in addition to effective components having pharmacological properties of a pharmaceutical composition, or added to maintain forms of liquid, etc. Examples of the excipient for maintaining a liquid form generally include saline, Hartman-D solution, PBS (phosphate buffered saline), etc., but may include other materials including various compositions.

As used herein, the term "adipose tissue-derived stem cell" is an undifferentiated stem cell isolated from an adipose tissue, and an isolation method thereof is as follows. The adipose tissue-derived stem cells may be isolated by a method of culturing a suspension containing adipose suspended in saline obtained by liposuction, treating a stem cell layer attached to a culture vessel with trypsin to recover the treated stem cells or recovering the stem cells by scraping using a scraper.

The stem cells of the present invention are capable of being obtained by the following method.

First, human adipose tissue obtained from the abdominal fat by liposuction is isolated and washed with PBS. Then, the isolated tissue is cut finely, decomposed by using DMEM media to which collagenase is added, and washed with PBS, followed by centrifugation. A supernatant is removed and pellets are washed with PBS, followed by centrifugation. Floating materials are removed using a 100 μm mesh, and the resulting cells are washed with PBS. The resulting cells are cultured in DMEM (10% FBS, 2 mM NAC, 0.2 mM ascorbic acid) media, and after one night, cells that are not adhered to a culture vessel are washed with PBS. Then, the remaining cells are subcultured while replacing the media with keratinocyte-SFM media (FBS, NAC, ascorbic acid, calcium, rEGF, insulin, bFGF and hydrocortisone) every other day, such that the adipose tissue-derived mesenchymal stem cells may be isolated. In addition to the above-described method, the stem cells may be obtained by methods previously known in the art.

In an exemplary embodiment of the present invention, the human adipose tissue-derived mesenchymal stem cells are suspended in a composition containing 10-50% (v/v) autologous or allogeneic human serum and 0.3% albumin or in a composition containing human blood plasma and 0.3% albumin, and then, sizes and properties of cells, the number of cells and survival rates thereof are analyzed depending on time in a refrigeration state (4° C.).

Therefore, according to an object of the present invention, there is provided a composition for improving cold-storage stability of stem cells containing blood serum or blood plasma having a content of 5 to 80% (v/v).

In the present invention, the content of the blood serum is preferably 10 to 50% (v/v), and the content of the blood plasma is preferably 5 to 50% (v/v), but each content thereof is not limited thereto.

The blood serum of the present invention is characterized by being blood serum or blood plasma derived from mammals including human. In addition, it is preferably blood serum or blood plasma derived from the same kind, and may be autologous serum or allogeneic serum or plasma without limitation.

In the present invention, the cold-storage preferably has a temperature range of 0.1 to 10° C., but the temperature range of the cold-storage is not limited thereto.

In the present invention, the composition for improving cold-storage stability of stem cells may further contain albumin and an excipient, wherein a content of the albumin is preferably 0.1 to 1% (v/v), more preferably, 0.2 to 0.5% (v/v), but the content of the albumin is not limited thereto. In addition, the excipient is preferably at least any one selected from the group consisting of saline, Hartmann-D solution and PBS, but is not limited thereto.

"v/v" means where total volume (volume percent) is made to be 100% by adding 1 to 80% of blood serum and 0.1 to 1% of albumin to volume (volume percent) of stem cells suspended in saline.

In the present invention, a concentration of the stem cells is preferably $1.0 \times 10^5$ to $1.0 \times 10^9$ cell/ml, and more preferably, $1.0 \times 10^6$ to $1.0 \times 10^8$ cell/ml, but the concentration of the stem cells is not limited thereto.

In the present invention, the stem cell is preferably selected from the group consisting of fat, cord blood, bone marrow, muscle, placenta and skin, and among them, the stem cell is the most preferably adipose tissue-derived stem cell, but the present invention is not limited thereto. In addition, the stem cell is characterized by being stem cells derived from mammal including human.

According to another object of the present invention, there is provided a cell therapeutic injection product containing a composition for improving cold-storage stability of stem cells containing blood serum or blood plasma.

The injection product according to the present invention may be prepared in an injection form filled in a content generally known in the art, the content varying depending on constitution and kinds of defects of patients.

The injection product according to the present invention may be injected in areas adjacent to defects to be treated or defect areas, and the defects that are capable of being corrected by this injection may be wrinkles, stretch marks, scars, skin depressions, lips forming dysfunction, periodontal defects, soft tissue defects, bone defects, burns, skin ulcers, etc. However, the kinds of the defects are not limited thereto.

In the present invention, if needed, the cell therapeutic injection product may further include suspending agents, solubilizing agents, stabilizers, isotonic agents, preservatives, adsorption inhibitors, surfactants, diluents, pH adjusting agents, soothing agents, buffering agents, sulfur-containing reducing agents, antioxidants, etc.

EXAMPLES

Hereinafter, the present invention will be described in more detail with reference to the following Examples. These examples are only for exemplifying the present invention, and it will be obvious to those skilled in the art that the scope of the present invention is not construed to be limited to these examples.

Example 1

Isolation and Culture of Human Adipose Tissue-derived Mesenchymal Stem Cell

Human adipose tissue obtained from an abdominal fat by liposuction was isolated and washed with PBS. The isolated tissue was cut finely and decomposed at 37° C. for 2 hours by using DMEM media to which collagenase type 1 (1 mg/ml) is added. The tissue treated with collagenase was washed with PBS and centrifuged at 1000 rpm for 5 minutes. A supernatant was removed and pellets were washed with PBS, followed by centrifugation at 1000 rpm for 5 minutes. Floating materials were removed by filtering using a 100 μm mesh, and the resulting cells were washed with PBS, and cultured in DMEM (10% FBS, 2 mM NAC (N-acetyl-Lcysteine) and 0.2 mM ascorbic acid) media. After one night, cells that were not adhered to a culture vessel were washed with PBS, and then, the cells were subcultured while replacing the media with keratinocyte-SFM media (5% FBS, 2 mM NAC, 0.2 mM ascorbic acid, 0.09 mM calcium, 5 ng/ml rEGF, 5 μg/ml insulin, 10 ng/ml bFGF and 74 ng/ml Hydrocortisone) every other day, such that the adipose tissue-derived mesenchymal stem cells were isolated.

Example 2

Constitution of Experimental Groups and pH Measurement for Each Excipient 2-1: Constitution of Experimental Groups Four different adipocyte stem cells isolated by the method of Example 1 were cold-stored at 4° C., and survival rates of the stem cells used for a refrigeration formulation cell therapeutic injection product were analyzed.

TABLE 1

| Stem cell | Control group | group 1 | group 2 | group 3 |
|---|---|---|---|---|
| cell 1 | 0.3% albumin | 0.3% albumin + 10% autologous human serum | 0.3% albumin + 20% autologous human serum | 0.3% albumin + 30% autologous human serum |
| cell 2 | | | | |
| cell 3 | 0.3% albumin | 0.3% albumin + 10% allogeneic human serum | 0.3% albumin + 20% allogeneic human serum | 0.3% albumin + 30% allogeneic human serum |
| cell 4 | | | | |

The four isolated adipocyte stem cells were used to constitute Experimental Groups as shown in Table 1. A stem cell Control Group containing 0.3% albumin, Experimental Group containing 0.3% albumin+10% autologous sera, Experimental Group containing 0.3% albumin+10% allogeneic sera, Experimental Group containing 0.3% albumin+20% autologous sera, Experimental Group containing 0.3% albumin+20% allogeneic sera, Experimental Group containing 0.3% albumin+30% autologous sera, and Experimental Group containing 0.3% albumin+30% allogeneic sera were constituted, and survival rates thereof were analyzed.

2-2: pH Values for Each Excipient

The pH of each excipient of the composition for improving storage stability of stem cells was analyzed in the present Example.

The pH is a numerical value of hydrogen ion concentration, and pH of general saline has a wide range of about 5.5 to 8.0. A pH change when albumin and human blood serum are added to saline was compared with PBS. The pH in a normal healthy state means a case in which cells, blood, body fluid, etc., are maintained to be weakly alkaline.

For the pH analysis, pH change by the albumin and human blood serum contained in the composition for improving storage stability of stem cells was analyzed by Orion Star A111 (Thermo Scientific Inc.). In addition, the pH was measured at room temperature ranging from 20° C. to 24° C. since it is affected by temperature.

TABLE 2

| | | | | pH measurement (SA:Saline + 0.3% Albumin) | | | | | |
|---|---|---|---|---|---|---|---|---|---|
| | | | | SA + 10% human serum | | SA + 20% human serum | | SA + 30% human serum | |
| | PBS | Saline | SA | serum 1 | serum 2 | serum 1 | serum 2 | serum 1 | serum 2 |
| 1st | 7.3 | 5.85 | 6.96 | 7.76 | 7.58 | 8.08 | 8.04 | 8.18 | 8.09 |
| 2nd | 7.3 | 5.93 | 6.88 | 7.82 | 7.57 | 8.27 | 8.05 | 8.2 | 8.07 |
| Avg | 7.3 | 5.89 | 6.92 | 7.79 | 7.57 | 8.17 | 8.04 | 8.19 | 8.08 |

As a result, it could be confirmed from Table 2 that the pH only slightly increased when only albumin was added, but maintained a weakly alkaline pH when the human blood serum was added.

After that, regarding this, viability of the stem cell Control Group suspended in saline containing 0.3% albumin, the stem cell Experimental Groups suspended in saline containing 10, 20, and 30% autologous human sera and 0.3% albumin, respectively, and the stem cell Experimental Groups suspended in saline containing 10, 20, and 30% allogeneic human sera and 0.3% albumin, respectively, was analyzed in Example 3.

Example 3

Analysis of Size and Properties of Stem Cell Depending on Time

The adipocyte stem cells isolated by the method of Example 1 were washed with PBS, and suspended in saline containing 0.3% albumin. Then, 10%, 20% and 30% autologous human sera and allogeneic human sera were added thereto, respectively, such that the resulting cells were constituted as Control Group and Experimental Groups of Example 2.

The stem cells for each Experimental Group having a concentration of $1.0 \times 10^7$ cell/ml were filled in 3 cc syringe and cold-stored at 4° C. After 0, 24, 48, 72, 96, 120 and 144 hours, sizes and properties of the stem cells used in the refrigeration formulation cell therapeutic injection product were analyzed.

3-1: Autologous Serum Experimental Groups

As to Cell 1, a Control Group in which $0.5 \times 10^7$ stem cells are suspended in saline containing 0.3% albumin, and three stem cell Experimental Groups in which $0.5 \times 10^7$ stem cells are suspended in saline containing 10, 20, and 30% autologous sera/0.3% albumin, respectively, were prepared.

As to Cell 2, a Control Group in which $1.0 \times 10^7$ stem cells are suspended in saline containing 0.3% albumin, and three stem cell Experimental Groups in which $1.0 \times 10^7$ stem cells are suspended in saline containing 10, 20, and 30% autologous sera/0.3% albumin, respectively, were prepared.

The stem cells of all of the Control Group and three Experimental Groups of Cell 1, and the Control Group and three Experimental Groups of Cell 2 were filled in 3 cc syringes, and cold-stored at 4° C. After 0, 24, 48, 72, 96, 120 and 144 hours, sizes and properties of the cells, and the total cell numbers were analyzed. The number of cells and sizes of the stem cells were analyzed by using Countess™ Automated Cell Counter (Invitrogen), and the properties thereof were analyzed with the naked eye.

TABLE 3

| | | | 0 hr | 24 hr | 48 hr | 72 hr | 96 hr | 120 hr | 144 hr |
|---|---|---|---|---|---|---|---|---|---|
| | Classification | | | | | Cell number ($\times 10^7$) | | | |
| cell 1 ($0.5 \times 10^7$ filling) | control | SA | 0.43 | 0.39 | 0.45 | 0.37 | 0.35 | 0.34 | 0.35 |
| | group 1 | SA + 10% human serum | 0.47 | 0.76 | 0.77 | 0.56 | 0.24 | 0.31 | 0.45 |
| | group 2 | SA + 20% human serum | 0.58 | 0.77 | 0.67 | 0.73 | 0.53 | 0.64 | 0.32 |
| | group 3 | SA + 30% human serum | 0.75 | 0.83 | 0.76 | 0.83 | 0.6 | 0.61 | 0.49 |

TABLE 4

| | | | 0 hr | 24 hr | 48 hr | 72 hr | 96 hr | 120 hr | 144 hr |
|---|---|---|---|---|---|---|---|---|---|
| | Classification | | | | | Cell size (μm) | | | |
| cell 1 ($0.5 \times 10^7$ filling) | control | SA | 16.05 | 15 | 15.03 | 14.12 | 12.9 | 12.98 | 11.65 |
| | group 1 | SA + 10% human serum | 15 | 15.5 | 15.92 | 15.6 | 14.44 | 14.27 | 13.37 |
| | group 2 | SA + 20% human serum | 14.3 | 15.53 | 15.45 | 15.16 | 14.25 | 14.61 | 13.82 |
| | group 3 | SA + 30% human serum | 14.1 | 15.4 | 15.04 | 14.86 | 14 | 14.39 | 13.69 |

TABLE 5

| Classification | | | 0 hr | 24 hr | 48 hr | 72 hr | 96 hr | 120 hr | 144 hr |
|---|---|---|---|---|---|---|---|---|---|
| | | | | | Cell number (×10$^7$) | | | | |
| cell 2 (1.0 × 10$^7$ filling) | control | SA | 1.3 | 1 | 0.85 | 0.75 | 0.65 | 0.69 | 0.8 |
| | group 1 | SA + 10% human serum | 1.3 | 0.98 | 0.89 | 0.69 | 0.56 | 0.56 | 0.51 |
| | group 2 | SA + 20% human serum | 1.1 | 1.1 | 0.98 | 0.89 | 0.79 | 0.72 | 0.53 |
| | group 3 | SA + 30% human serum | 0.97 | 1.1 | 0.99 | 1 | 0.91 | 0.72 | 0.6 |

TABLE 6

| Classification | | | 0 hr | 24 hr | 48 hr | 72 hr | 96 hr | 120 hr | 144 hr |
|---|---|---|---|---|---|---|---|---|---|
| | | | | | Cell size (μm) | | | | |
| cell 2 (1.0 × 10$^7$ filling) | control | SA | 17.3 | 16.14 | 16.23 | 16.06 | 15.9 | 16.27 | 15.08 |
| | group 1 | SA + 10% human serum | 16.99 | 15.69 | 15.6 | 15.39 | 15.36 | 15.2 | 15.21 |
| | group 2 | SA + 20% human serum | 16.72 | 15.37 | 15.21 | 15.18 | 15.06 | 15.28 | 15.03 |
| | group 3 | SA + 30% human serum | 16.3 | 15.28 | 15.24 | 15.15 | 14.82 | 15.01 | 14.9 |

The results thereof were shown in Table 3 (the number of cells of Cell 1), Table 4 (size of Cell 1), Table 5 (the number of cells of Cell 2), and Table 6 (size of Cell 2).

As shown in Tables 3 to 6, the cell size of the Control Group was reduced by about 15 to 25%; meanwhile, the cell size of the Experimental Groups containing autologous human sera was reduced by about 3 to 10%, such that a change in cell size was not significant in Experimental Groups containing autologous human sera. Meanwhile, changes in the properties of cells of the Control Group and the Experimental Groups were not observed, and there was no difference in the total cell number among Control Group and Experimental Groups.

3-2: Allogeneic Serum Experimental Groups

As to Cell 3, a Control Group in which 0.5×10$^7$ stem cells are suspended in saline containing 0.3% albumin, and three stem cell Experimental Groups in which 0.5×10$^7$ stem cells are suspended in saline containing 10, 20, and 30% allogeneic sera/0.3% albumin, respectively, were prepared.

As to Cell 4, a Control Group in which 1.0×10$^7$ stem cells are suspended in saline containing 0.3% albumin, and three stem cell Experimental Groups in which 1.0×10$^7$ stem cells are suspended in saline containing 10, 20, and 30% allogeneic sera/0.3% albumin, respectively, were prepared.

The stem cells of all of the Control Group and three Experimental Groups of Cell 3, and the Control Group and three Experimental Groups of Cell 4 were filled in 3 cc syringes, and cold-stored at 4° C. After 0, 24, 48, 72, 96, 120 and 144 hours, sizes and properties of the cells, and the total cell numbers were analyzed. The number of cells and sizes of the stem cells were analyzed by using Countess™ Automated Cell Counter (Invitrogen), and the properties thereof were analyzed with the naked eye.

TABLE 7

| Classification | | | 0 hr | 24 hr | 48 hr | 72 hr | 96 hr | 120 hr | 144 hr |
|---|---|---|---|---|---|---|---|---|---|
| | | | | | Cell number (×10$^7$) | | | | |
| cell 3 (0.5 × 10$^7$ filling) | control | SA | 0.46 | 0.64 | 0.63 | 0.54 | 0.5 | 0.42 | 0.14 |
| | group 1 | SA + 10% human serum | 0.66 | 0.65 | 0.56 | 0.42 | 0.33 | 0.23 | 0.28 |
| | group 2 | SA + 20% human serum | 0.45 | 0.64 | 0.55 | 0.49 | 0.4 | 0.25 | 0.29 |
| | group 3 | SA + 30% human serum | 0.49 | 0.61 | 0.61 | 0.5 | 0.46 | 0.33 | 0.29 |

TABLE 8

| Classification | | | 0 hr | 24 hr | 48 hr | 72 hr | 96 hr | 120 hr | 144 hr |
|---|---|---|---|---|---|---|---|---|---|
| | | | | | Cell size (μm) | | | | |
| cell 3 (0.5 × 10$^7$ filling) | control | SA | 16.15 | 15.92 | 14.79 | 13.35 | 13.46 | 13.8 | 13.14 |
| | group 1 | SA + 10% human serum | 15.45 | 15.87 | 15.3 | 14.79 | 14.61 | 14.16 | 13.34 |
| | group 2 | SA + 20% human serum | 14.08 | 15.34 | 14.83 | 14.72 | 14.66 | 14.21 | 14.06 |

TABLE 8-continued

| Classification | | 0 hr | 24 hr | 48 hr | 72 hr | 96 hr | 120 hr | 144 hr |
|---|---|---|---|---|---|---|---|---|
| | | | | Cell size (μm) | | | | |
| group 3 | SA + 30% human serum | 13.8 | 15.1 | 14.83 | 14.67 | 14.54 | 13.75 | 13.45 |

TABLE 9

| | Classification | | 0 hr | 24 hr | 48 hr | 72 hr | 96 hr | 120 hr | 144 hr |
|---|---|---|---|---|---|---|---|---|---|
| | | | | | Cell number (×10$^7$) | | | | |
| cell 4 ($1.0 \times 10^7$ filling) | control | SA | 0.92 | 0.68 | 0.68 | 0.67 | 0.7 | 0.54 | 0.5 |
| | group 1 | SA + 10% human serum | 0.83 | 0.9 | 0.76 | 0.62 | 0.69 | 0.5 | 0.45 |
| | group 2 | SA + 20% human serum | 0.75 | 0.88 | 0.87 | 0.78 | 0.74 | 0.67 | 0.51 |
| | group 3 | SA + 30% human serum | 0.67 | 0.87 | 0.92 | 0.86 | 0.84 | 0.7 | 0.58 |

TABLE 10

| | Classification | | 0 hr | 24 hr | 48 hr | 72 hr | 96 hr | 120 hr | 144 hr |
|---|---|---|---|---|---|---|---|---|---|
| | | | | | Cell size (μm) | | | | |
| cell 4 ($1.0 \times 10^7$ filling) | control | SA | 16.47 | 16.72 | 15.9 | 15.9 | 16.42 | 15.78 | 16.39 |
| | group 1 | SA + 10% human serum | 16.55 | 16.08 | 15.78 | 15.83 | 16.46 | 15.75 | 16.07 |
| | group 2 | SA + 20% human serum | 16.27 | 15.59 | 15.31 | 15.55 | 15.53 | 15.13 | 15.37 |
| | group 3 | SA + 30% human serum | 16.05 | 15.41 | 15.14 | 14.94 | 15.3 | 15.03 | 15.1 |

The results thereof were shown in Table 7 (the number of cells of Cell 3), Table 8 (size of Cell 3), Table 9 (the number of cells of Cell 4), and Table 10 (size of Cell 4).

As shown in Tables 7 to 10, the cell size of the Control Group was reduced by about 20%; meanwhile, the cell size of the Experimental Groups containing allogeneic human sera was reduced by about 3 to 10%, such that a change in cell size was not significant in Experimental Groups containing allogeneic human sera. Meanwhile, changes in the properties of cells of the Control Group and the Experimental Groups were not observed, and there was no difference in total cell number among Control Group and Experimental Groups.

Example 4

Analysis of Survival Rate of Stem Cell Depending on Time

Survival rates of the stem cells depending on time were analyzed by the same condition as Example 3.

The isolated adipocyte stem cells were washed with PBS, and suspended in saline containing 0.3% albumin. Then, 10%, 20% and 30% autologous human sera and allogeneic human sera were added thereto, respectively, such that the resulting cells were constituted as the Control Group and Experimental Groups, respectively. The stem cells for each Experimental Group having a concentration of $1.0 \times 10^7$ cell/ml were filled in 3 cc syringes and cold-stored at 4° C. After 0, 24, 48, 72, 96, 120 and 144 hours, survival rates of the stem cells used in the refrigeration formulation cell therapeutic injection product were analyzed. The survival rates of the stem cell were measured by mixing the cells and trypan blue solution at a ratio of 1:1 and analyzed by Countess™ Automated Cell Counter (Invitrogen).

As a result, it was confirmed in the compositions containing human sera that a survival rate was high without significant change in the number of cells, and as a serum concentration was increased, the survival rate was also increased, and a retention period for cell stability also became longer, as compared to the Control Group containing 0.3% albumin only. (FIGS. 1, 2, 3, and 4).

Figure 3:
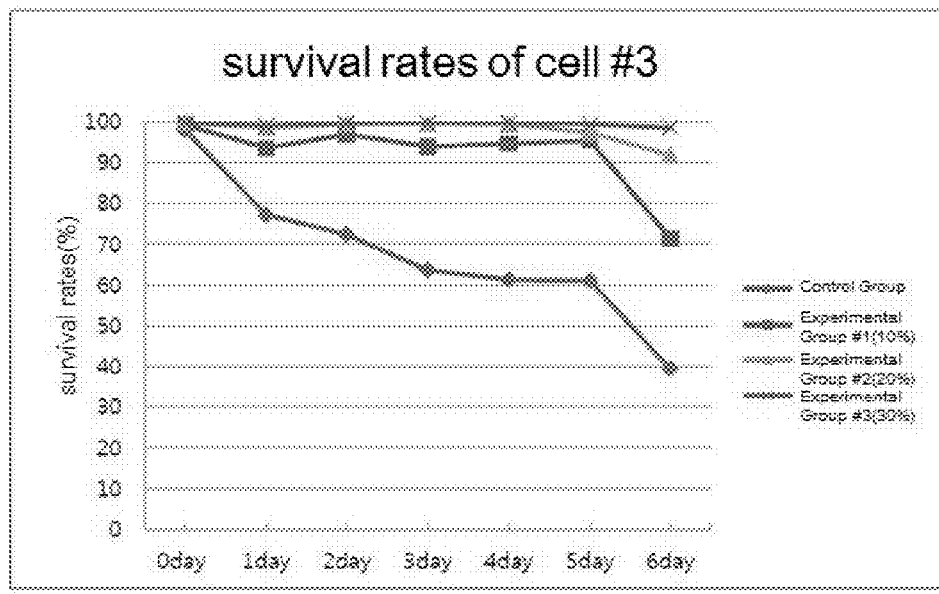
FIG. 3 illustrates comparison of survival rates of $0.5 \times 10^7$ stem cells according to the retention time from 0 to 144 hours, after cold-storage of the stem cells with different concentrations (10, 20, and 30%) of allogeneic sera and preservative containing 0.3% albumin. The Control Group used a preservative containing 0.3% albumin.
Figure 4:
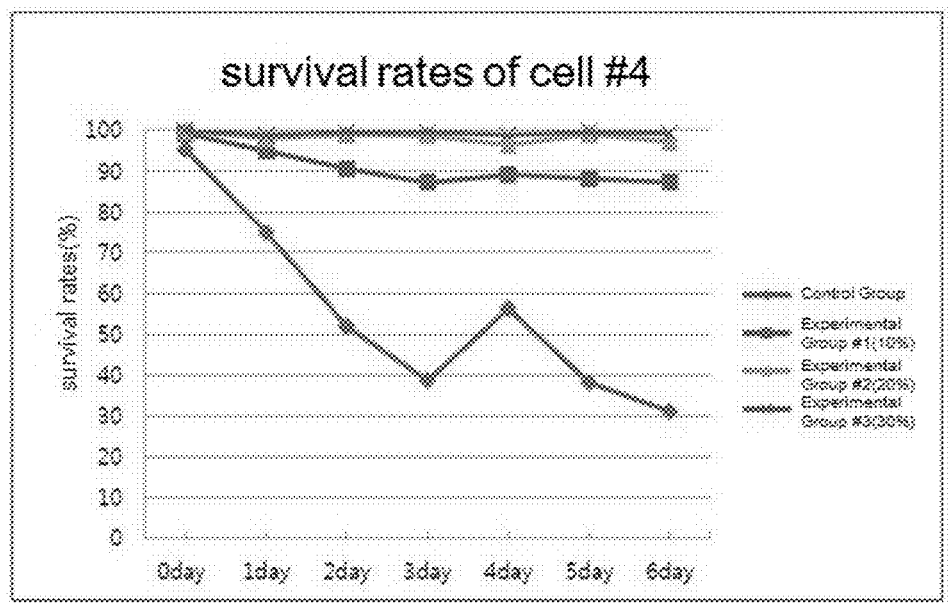
FIG. 4 illustrates comparison of survival rates of $1.0 \times 10^7$ stem cells according to the retention time from 0 to 144 hours, after cold-storage of the stem cells with different concentrations (10, 20, and 30%) of allogeneic sera and a preservative containing 0.3% albumin. The Control Group used a preservative containing 0.3% albumin.

In particular, it was confirmed that Experimental Group 3 which is stem cells containing 30% blood serum maintained 98% or more of significant high cell survival rate up to 144 hours, and that even Experimental Group containing 10 to 20% blood serum exhibited 90% or more up to 72 hours. Further, there was no difference in effect of survival rate depending on retention time of cells between autologous serum Experimental Groups (FIGS. 1 and 2) and allogeneic serum Experimental Groups (FIGS. 3 and 4).

Accordingly, it was confirmed that the composition for improving storage stability of stem cells by the human serum could maintain a long-term survival rate of 144 hours or more, and there was no difference in effects between autologous serum and allogeneic serum.

Example 5

Constitution of New Experimental Groups

After it was confirmed that there was no difference in effects between autologous serum and allogeneic serum in the Example, Experimental Groups were constituted to examine cell stability depending on each blood serum concentration and blood plasma.

A Control Group (SA: Saline+0.3% Albumin) and six Experimental Groups including various blood serum concentrations (10 to 50%) or blood plasma (PRP) were shown in Table 11, and cell cold-storage stability thereof was measured up to Day 9.

TABLE 11

| Lot No. | control | group 1 | group 2 | group 3 | group 4 | group 5 | group 6 |
|---|---|---|---|---|---|---|---|
| cell 1 | SA | SA + pH buffer (pH 8.2) | 10% serum 1 + SA | 30% serum 1 + Saline | 30% serum 1 + SA | 50% serum 1 + SA | 10% PRP 1 + SA |
| cell 2 | | | 10% serum 2 + SA | 30% serum 2 + Saline | 30% serum 2 + SA | 50% serum 2 + SA | 10% PRP 2 + SA |

5-1: Stem Cell

Two different adipocyte stem cells isolated by the method of Example 1 were cold-stored at 4° C., and survival rates of the stem cells used for a refrigeration formulation cell therapeutic injection product were analyzed.

The respective stem cells were prepared in a content of $4.9 \times 10^8$ cells (specifically, the number of $1.0 \times 10^7$ cells/ml is 49). Two subcultured cells thawed ($6.0 \times 10^6$ cells thawed in 5 T175 flasks), and cultured (3 subcultured $4.9 \times 10^7$ cells were cultured in 49 T175 flasks), and the cells were recovered ($4.9 \times 10^8$ cells) at fourth subculture, and filled and experimented.

The cells recovered at the fourth subculture were divided into 7 tubes each having $7.0 \times 10^7$ cells, and mixed with 7 preservatives (7 ml) shown in Table 11. Then, the cells were filled in 7 syringes (3 cc) each having 1 ml of cells on Days 0, 1, 2, 3, 5, 7, and 9 for each Experimental Group (preservative). For the sample on Day 0, the number of cells, the survival rate, and the cell size were directly measured, and for the remaining samples, the number of cells, the survival rate, and the cell size Cedex were measured after cold-storing for 1, 2, 3, 5, 7 and 9 days.

5-2: Blood Serum and Blood Plasma

In order to isolate blood serum, blood (10 ml) was collected by using a blood collection tube without containing anticoagulant and placed upright in a refrigeration state for 10 minutes. Centrifugation was performed with brake off at 1000 RCF for 15 minutes to remove fibrin, and then, blood serum which is an isolated supernatant, was recovered. The recovered blood serum was subjected to centrifugation with brake off at 1700 rpm for 5 minutes, and the supernatant was collected and prepared by sterilization using a 0.2 μm syringe filter.

In order to isolate blood plasma, an anticoagulant (2 cc) was injected into a syringe (20 cc), and blood was collected. Then, blood plasma and erythrocytes were primarily isolated by Dr.PRP kit, followed by centrifugation at 3200 rpm for 6 minutes, to condense platelets, and the remaining materials were secondarily isolated. After secondary isolation, the above PPP (4 ml) was slowly removed with 10 cc syringe in a state in which PRP (blood plasma containing platelets) and PPP (blood plasma without containing platelets) were isolated, and the remaining PRP (4 ml) was well mixed to be used.

5-3: pH of Excipient

As practiced in Example 2-2, pH of excipients of the compositions for improving storage stability of stem cells for each Experimental Group was analyzed.

For the pH analysis, pH change by the albumin and human blood serum contained in the composition for improving storage stability of stem cells was analyzed by Orion Star A111 (Thermo Scientific Inc.).

TABLE 12 pH measurement (SA: Saline + 0.3% Albumin)

| S | SA | SA + pH buffer | 10% PRP + SA | 10% Serum + SA | 30% Serum + Saline | 30% Serum + SA | 50% Serum + SA |
|---|---|---|---|---|---|---|---|
| cell 1 | 5.6 | 6.60 | — | — | 7.71 | 8.07 | 8.06 | 8.05 |
| cell 2 | 5.38 | 6.62 | — | — | 8.0 | 7.99 | 7.96 | 8.08 |
| Avg | 5.49 | 6.61 | 8.2 | — | 7.85 | 8.03 | 8.01 | 8.06 |

As a result, an average pH value of the storage stabilizers of stem cells containing blood serum added thereto was measured to be 8.2, and pH of saline (pH=7.3) was determined to be 8.2 by using 8.4% sodium bicarbonate ($NaHCO_3$) as a pH buffer. In the case of blood plasma, since an amount was significantly small, it was impossible to measure the pH.

Example 6

Changes in the Number of Cells, Survival Rate and Size of Stem Cells Depending on Time The adipocyte stem cells isolated by the method of Example 1 were washed with PBS, and prepared by the same method as in Example 5-1. Two kinds of adipocyte stem cells were constituted as the Control Group and six Experimental Groups as shown in Table 11, and the number of cells, survival rate, and cell size thereof were examined up to Day 9.

As a result, it was confirmed that the Control Group (SA: Saline+0.3% albumin) without containing blood serum or blood plasma maintained about 80% survival rate up to Day 3. However, the Experimental Groups containing 10% blood plasma or 10% blood serum exhibited a survival rate increased up to 50% or more as compared to the Control Group (FIGS. 5 and 6).

Figure 5:
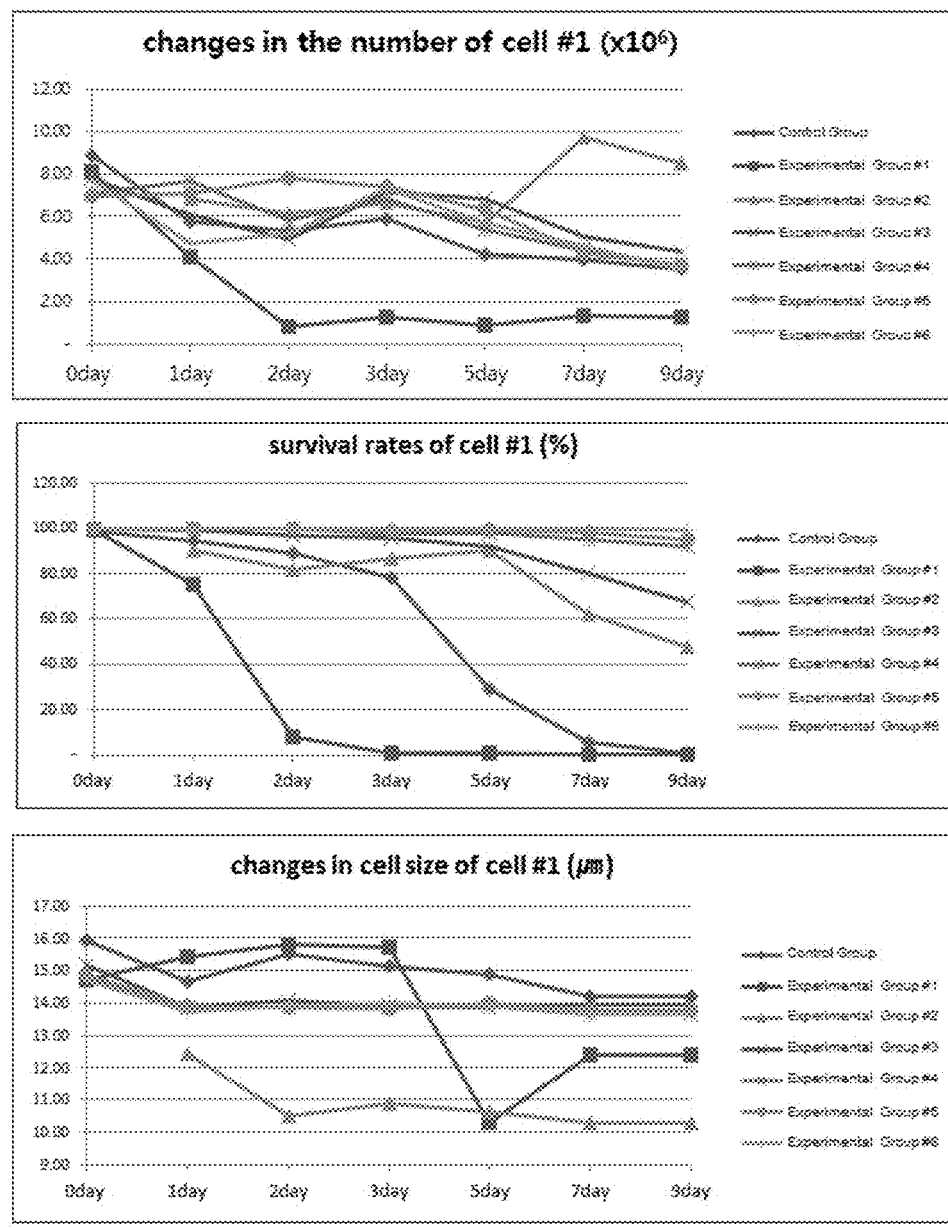
FIG. 5 illustrates comparison results of changes in the number of cells, survival rates, and cell sizes of a Control Group (saline/0.3% albumin) of stem cell #1 and compositions for improving storage stability corresponding to Experimental Groups (1 to 6) each having a different condition.
Figure 6:
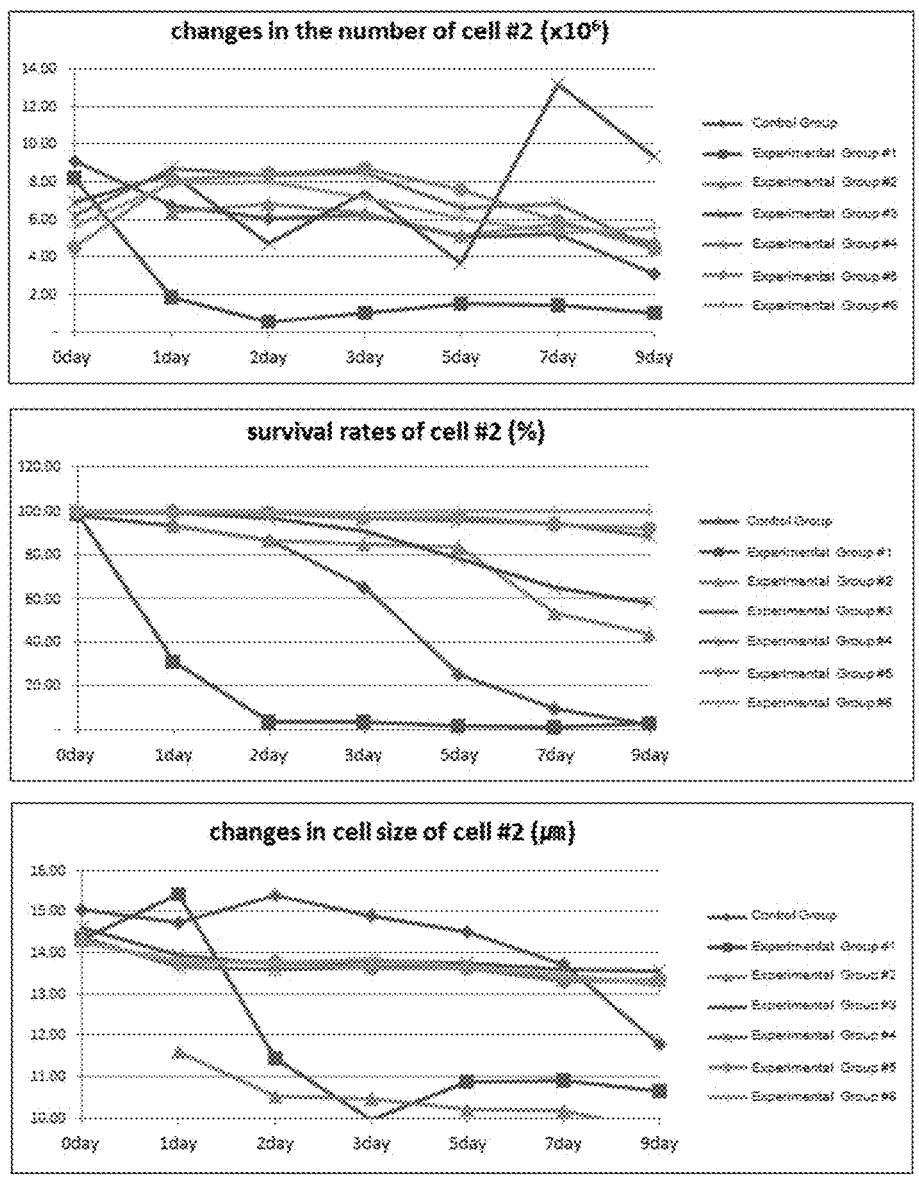
FIG. 6 illustrates comparison results of the number of cells, a survival rate and a change in cell size of a Control Group (saline/0.3% albumin) of stem cell #2 and compositions for improving storage stability corresponding to Experimental Groups (1 to 6) each having a different condition.

It could be confirmed that the cell survival rate was the highest when the concentration of the blood serum is 50%, but 90% or more of cell survival rate was exhibited up to Day 9 in the Experimental Group containing 30% blood serum (FIGS. 5 and 6).

Therefore, it was confirmed that when the stem cells were cold-stored by using the preservative containing the blood serum or the blood plasma, the storage stability of the stem cells was improved, such that it was possible to store the stem cells for a long period of time without changes in the number of cells, survival rate, and cell size.

Example 7

Comparison on Storage Stabilizers of Stem Cells

As analysis result of survival rate of stem cell #1 (FIG. 5) and stem cell #2 (FIG. 6) in Example 6, it was found that difference between Cell 1 and Cell 2 was rarely shown, and accordingly, effects for each stabilizer with regard to Cell 1 were analyzed in Example 7.

Figure 7:
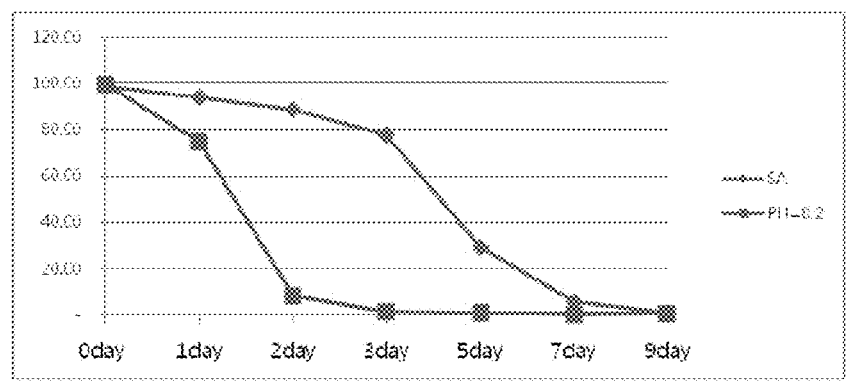
FIG. 7 illustrates effects of the pH of a preservative with regard to a cell survival rate.

In order to examine an effect of pH which is one of the factors having an effect on the storage stabilizer of stem cells, sodium bicarbonate ($NaHCO_3$) was used as a pH buffer, and pH of the stabilizer was determined to be 8.2. As a result, cell-survival time of the Control Group (SA: Saline+0.3% albumin) was the maximum of 1 day (FIG. 7). Accordingly, it was found that the stabilizer of which the pH value was determined as 8.2 had no effect on promotion of cell stability.

Figure 8:
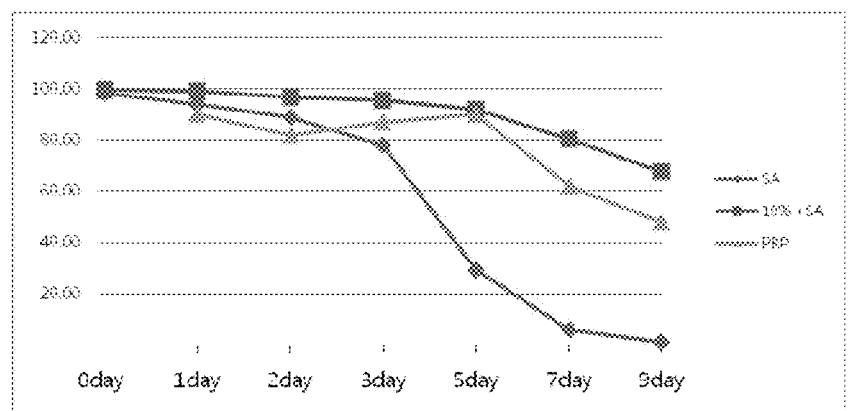
FIG. 8 illustrates comparison results of effects of blood serum and blood plasma with regard to cell viability.

Next, the effects of blood serum and blood plasma were compared with each other. It could be appreciated that in the stabilizer containing 10% blood serum or 10% blood plasma, the survival rate was increased up to 50% or more as compared to the Control Group, and it was confirmed that the difference between the blood serum and the blood plasma was not significant, but stability in a similar trend was exhibited (FIG. 8).

Figure 9:
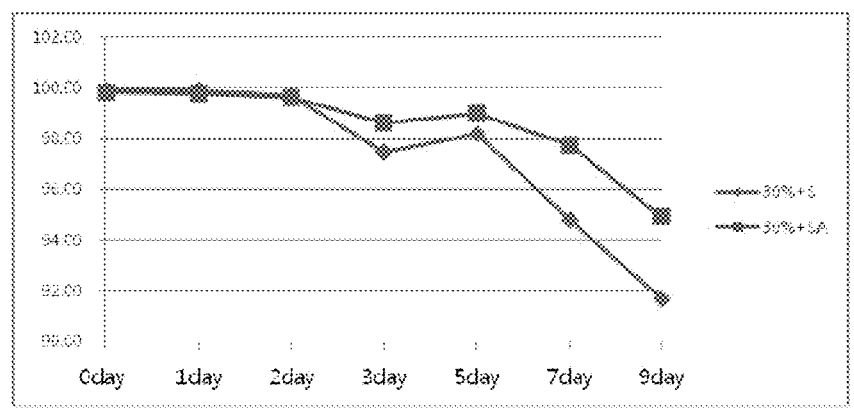
FIG. 9 illustrates effects of albumin with regard to cell viability.

In order to appreciate the effect of albumin contained in the stabilizer, storage stability of stem cells using 30% blood serum/saline and 30% blood serum/SA (saline+0.3% albumin) was examined. As a result, it was confirmed that when 0.3% albumin is included, cell stability was slightly higher (FIG. 9). However, it could be appreciated that the difference between two Experimental Groups was not significant up to Day 9, such that the mixing of the blood serum and albumin did not have a significant effect on the effect of the stabilizer.

Figure 10:
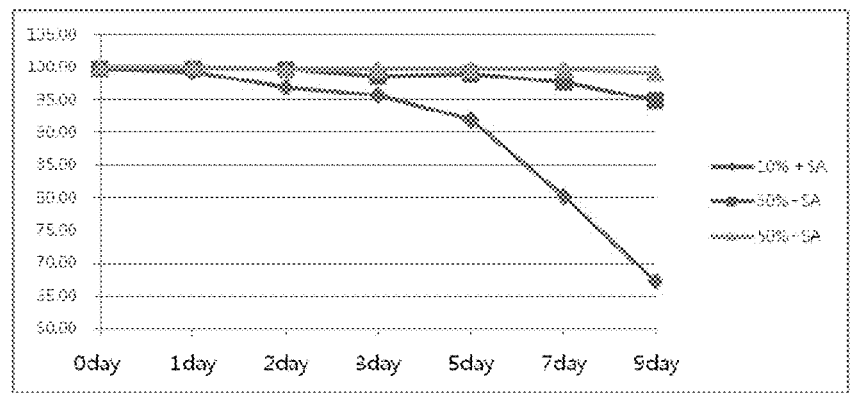
FIG. 10 illustrates comparison results of effects of blood serum concentration with regard to cell viability.

Accordingly, the storage stability of the stem cells was compared by increasing the concentration of the blood serum as a method for improving the effect of the storage stabilizer. As a result obtained by measuring the survival rate after the concentration of the blood serum is increased to be 10, 30, and 50% in the blood serum/SA (saline+0.3% albumin) Experimental Group, the stabilizer containing 50% blood serum exhibited the highest survival rate. In addition, it was confirmed that 80% or more of survival rate was maintained for 7 days even in the stabilizer containing 10% blood serum, and 90% or more of the very high survival rate was exhibited for 9 days even in the stabilizer containing 30% blood serum (FIG. 10). This confirmation indicated that the blood serum had a significant function for maintaining the survival rate of cells in a refrigeration state.

INDUSTRIAL APPLICABILITY

The composition for promoting cold-storage stability of stem cells according to the present invention is capable of maintaining a survival rate over 90% for at least 9 days without changes in the number of stem cells, and properties and sizes of the stem cells, which is useful for long-term transport of stem cells for cell therapy and the preparation of cell therapeutics injection products having an excellent effect.

The specific embodiments of the present invention are described in detail as set forth above. However, it will be apparent to those skilled in the art that the specific description is merely desirable exemplary embodiment and should not be construed as limiting the scope of the present invention. Therefore, the substantial scope of the present invention will be defined by the accompanying claims and their equivalents.

The invention claimed is:

1. A method for improving cold-storage stability of stem cells, the method comprising:
   (i) suspending the stem cells in a composition consisting of blood serum and excipient,
   wherein the content of the blood serum in the composition is 5-80%(v/v),
   wherein the excipient is at least any one selected from the group consisting of saline, Hartmann solution, and PBS; and
   (ii) storing the stem cells at cold-storage temperature, wherein the temperature range of cold-storage is 0.1 to 10° C.,
   wherein the composition is free of fibrinogen and anticoagulant.

2. The method of claim 1, wherein the content of the blood serum is 10 to 50%(v/v).

3. The method of claim 1, wherein the composition is for intravascular administration.

4. A method for improving cold-storage stability of stem cells, the method comprising:
   (i) suspending the stem cells in a composition consisting of blood serum, albumin, and excipient,
   wherein the content of the blood serum in the composition is 5-80%(v/v),
   wherein the excipient is at least any one selected from the group consisting of saline, Hartmann solution, and PBS; and
   (ii) storing the stem cells at cold-storage temperature, wherein the temperature range of cold-storage is 0.1 to 10° C.,
wherein the composition is free of fibrinogen and anticoagulant.

* * * * *